US006242424B1

(12) United States Patent
Riess et al.

(10) Patent No.: US 6,242,424 B1
(45) Date of Patent: Jun. 5, 2001

(54) MOENOMYCIN AND ITS DERIVATIVES FOR THE PRODUCTION OF PHARMACEUTICALS, AND PHARMACEUTICALS CONTAINING MOENOMYCIN OR ITS DERIVATIVES

(75) Inventors: Günther Riess, Hattersheim; Gerhard Seibert, Darmstadt; Udo Hedtmann, Frankfurt, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 08/348,815

(22) Filed: Nov. 28, 1994

(30) Foreign Application Priority Data

Nov. 30, 1993 (DE) ................................. 43 40 774

(51) Int. Cl.$^7$ ................................. A61K 31/70
(52) U.S. Cl. .................... 514/25; 514/53; 536/16.8; 536/17.2
(58) Field of Search ............... 514/25, 53; 536/16.8, 536/17.2

(56) References Cited

U.S. PATENT DOCUMENTS 4,684,626 * 8/1987 Welzel et al. ..................... 514/53

OTHER PUBLICATIONS

Heβler–Klintz et al., *The First Moenomycin Antibiotic Without the Methyl–Branched Uronic Acid Constituent. Unexpected Structure Activity Relations*, Tetrahedron, vol. 49 (35): 7667–7678 (1993).

G. Huber, *Moenomycin and Related Phosphorus–Containing Antibiotics*, "Antibiotics", ed. F. Hahn, Springer Verlag, Berlin, 1979, vol. IV, pp. 135 ff.

Welzel et al., *Moenomycin A: Further Structural Studies and Preparation Of Simple Derivatives*, Tetrahedron, vol. 39 (9) : 1583–1591 (1983).

A.T.R. Axon, *Helicobacter Pylori Infection*, J. Antimicrob. Chemother. 32, Suppl. A., 61–68 (1993).

* cited by examiner

*Primary Examiner*—Elli Peselev
(74) *Attorney, Agent, or Firm*—Finnegan, Henderson, Farabow, Garrett and Dunner, L.L.P.

(57) ABSTRACT

Moenomycin and its derivatives are suitable for the production of pharmaceuticals for the treatment of gastric ulcers and for the control of *Helicobacter pylori*.

2 Claims, No Drawings

MOENOMYCIN AND ITS DERIVATIVES FOR THE PRODUCTION OF PHARMACEUTICALS, AND PHARMACEUTICALS CONTAINING MOENOMYCIN OR ITS DERIVATIVES

The present invention relates to moenomycin and its derivatives for the production of pharmaceuticals, and pharmaceuticals containing moenomycin or its derivatives.

The present invention is based on the object of finding an effective medicament for the control of gastric ulcers and for the prophylaxis of cancer of the stomach. Hitherto, e.g. so-called antacids and, with particular success, $H_2$-receptor blockers were used in the indication area mentioned.

Furthermore, it was already known that Helicobacter pylori infections are frequently responsible for stomach disorders. Infection of the human stomach with the pathogenic gram-negative bacterium *Helicobacter pylori* causes temporary dyspeptic symptoms. *H. pylori* is additionally the underlying pathogen in the chronically active type b gastritis and a significant risk factor for the occurrence of cancer of the stomach. The pathophysiological mechanisms by which *H. pylori* causes diseases of the stomach are still relatively unclear. It is known that the microorganism produces a number of potentially toxic enzymes and chemicals (urease, ammonia, vacuolizing cytotoxin). The persistence of the bacterium and the lasting antigenic stimulus are probably the cause of the long-term destruction of the gastric mucous membrane.

The therapeutic aim is the complete eradication of *H. pylori*. The therapy of choice at the moment is a triple combination which consists of a bismuth salt, metronidazole and amoxicillin or tetracycline. However, it has some serious side effects. These include exhaustion, dryness of the mouth, diarrhea and nausea. The patient must additionally give up alcohol during therapy. Even with good compliance, eradication rates of only about 90% are achieved (A.T.R. Axon, 1993, J. Antimicrob. Chemother. 32, Suppl. A, 61 to 68).

Surprisingly, it has now been found that moenomycin is outstandingly effective against all previously investigated *Helicobacter pylori* strains. This is particularly surprising, because until now moenomycin was known to be almost exclusively effective against gram-positive microorganisms (Welzel et al., 1983, Tetrahedron Vol. 39, No. 9, 1583 to 1591).

The invention accordingly relates to the use of moenomycin and/or one or more of its derivatives for the production of a pharmaceutical for the control of gastric ulcers and for the prophylaxis of cancer of the stomach, and generally the use of moenomycin and/or one or more of its derivatives for the production of a pharmaceutical for the control of *Helicobacter pylori* infections.

Moenomycin and many of its derivatives have already been known for a long time (cf. German Offenlegungsschrift 3,704,659, EP 0,355,679, G. Huber in "Antibiotics", ed. F. Hahn, Springer Verlag, Berlin 1979, Vol. IV, page 135 ff., Welzel et al. in Tetrahedron loc. cit.). Moenomycins, e.g. moenomycin A, are preferably obtained by fermentation of microorganisms and subsequent purification.

The term moenomycin in the sense of the present patent application is to be understood as meaning a complex of moenomycin components (e.g. as is formed by microorganisms) and also the individual components. This means that the moenomycin can be administered in the form of one or more components in a variable composition. The administration of the largely pure particularly effective individual components, in particular of moenomycin A, is preferred. Said moenomycin A has the following structural formula:

1

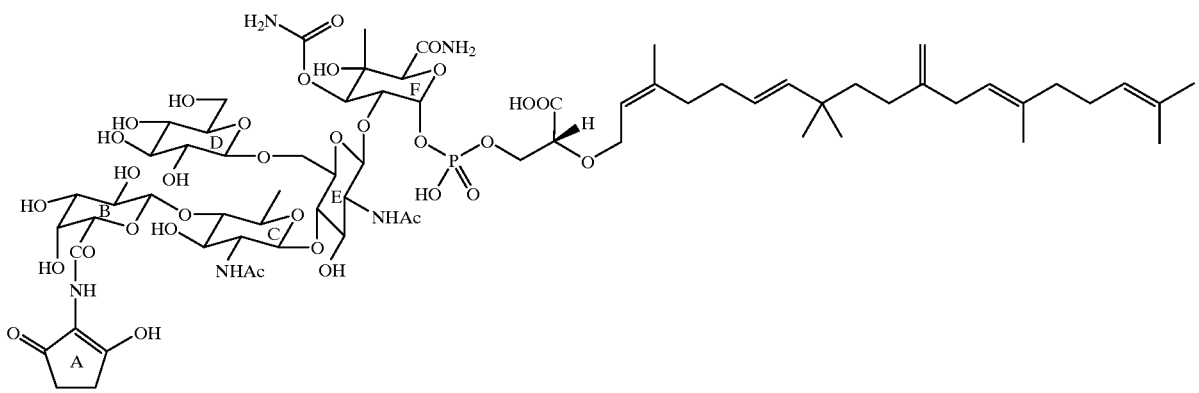

Microorganisms which produce moenomycin complexes are e.g. *Streptomyces bambergiensis, ghanaensis, ederensis* and *geysirensis. Streptomyces bambergiensis* is particularly preferred (cf. in this connection Huber loc. cit.). The term "derivatives of moenomycin" should generally be taken hitherto and in future to mean synthesized moenomycin derivatives. Particularly suitable moenomycin components or derivatives of moenomycin are the compounds of the following formulae

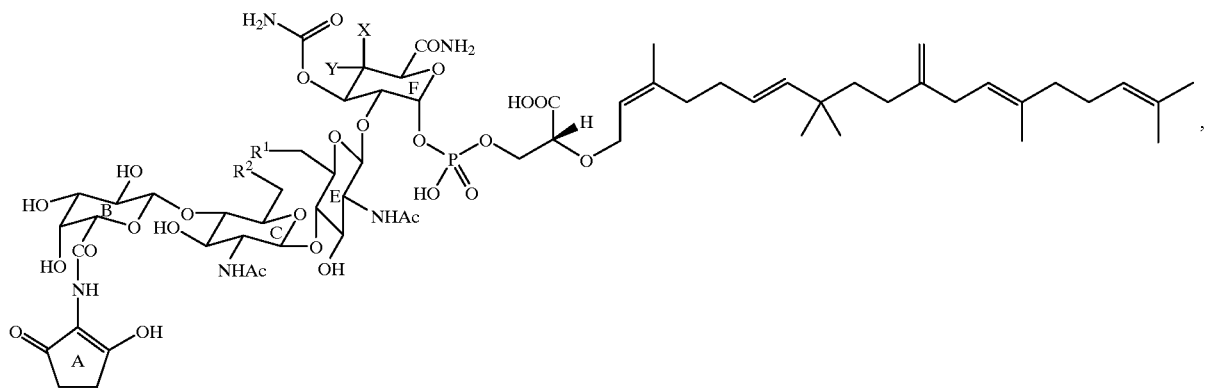
in which the individual substituents have the following meanings,
|   | X | Y | R¹ | R² |
|---|---|---|---|---|
| 1 | $CH_3$ | OH | (sugar: $CH_2OH$, HO, HO, OH) | H |
| 3 | $CH_3$ | OH | H | H |
-continued
|   | X | Y | R¹ | R² |
|---|---|---|---|---|
| 4 | $CH_3$ | OH | OH | H |
| 5 | $CH_3$ | OH | OH | OH |
| 6 | OH | H | H | H |
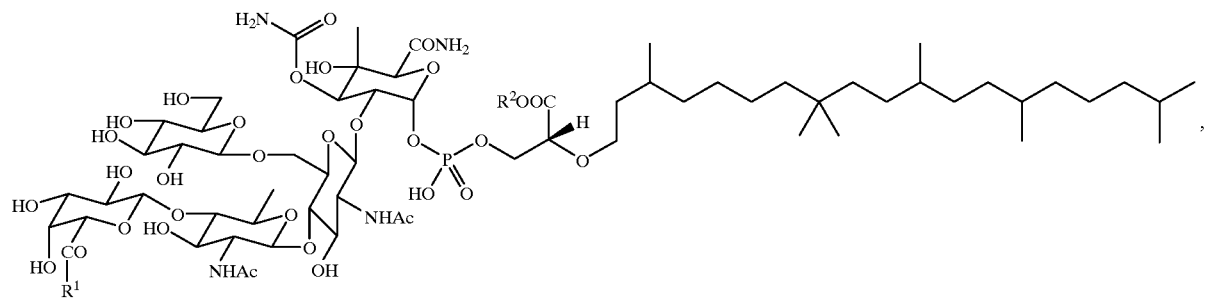
in which $R_1$ and $R_2$ have the following meanings,
|   | R¹ | R² |
|---|---|---|
| 7 | (2-amino-3-hydroxycyclopent-2-enone: NH, OH, O) | H |
| 8 | $NH_2$ | H |
| 9 | $NH_2$ | $CH_3$ |

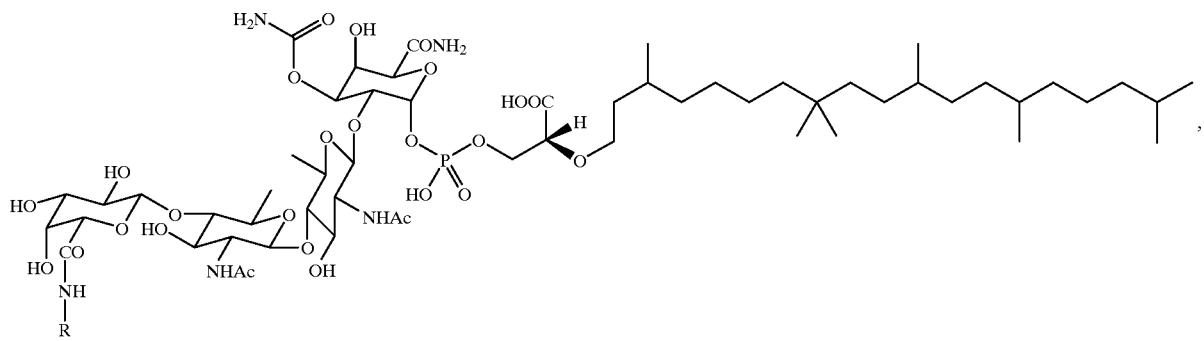
in which R is hydrogen or
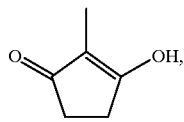
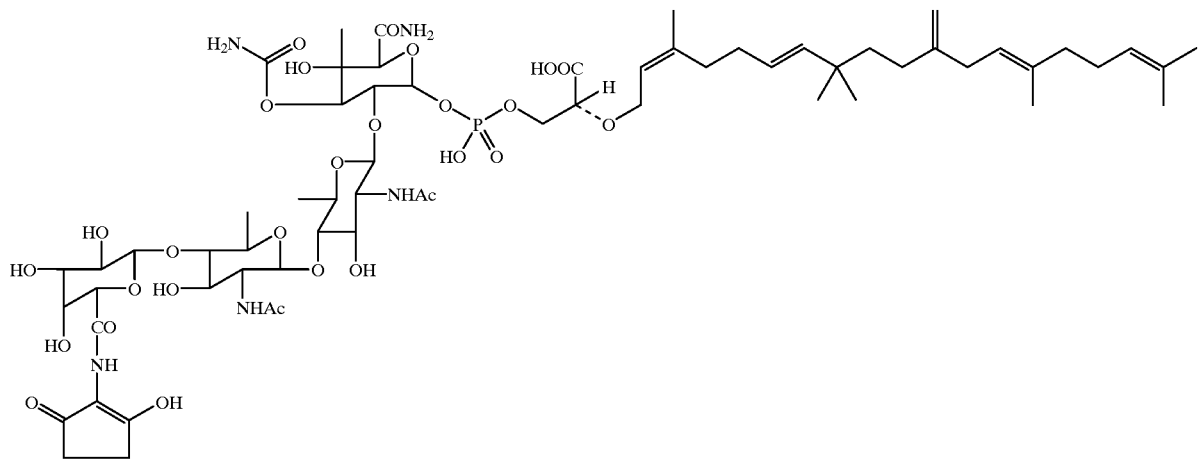
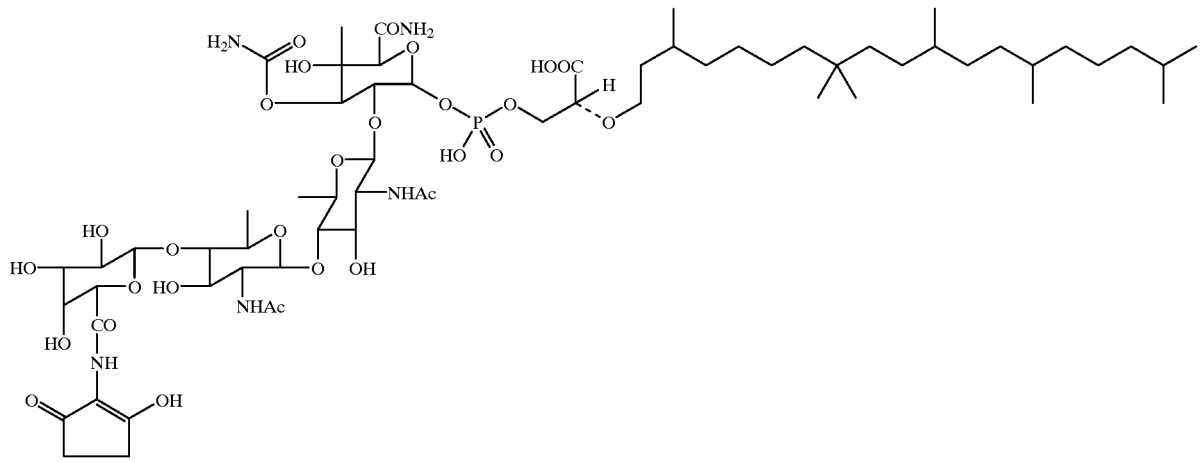

-continued

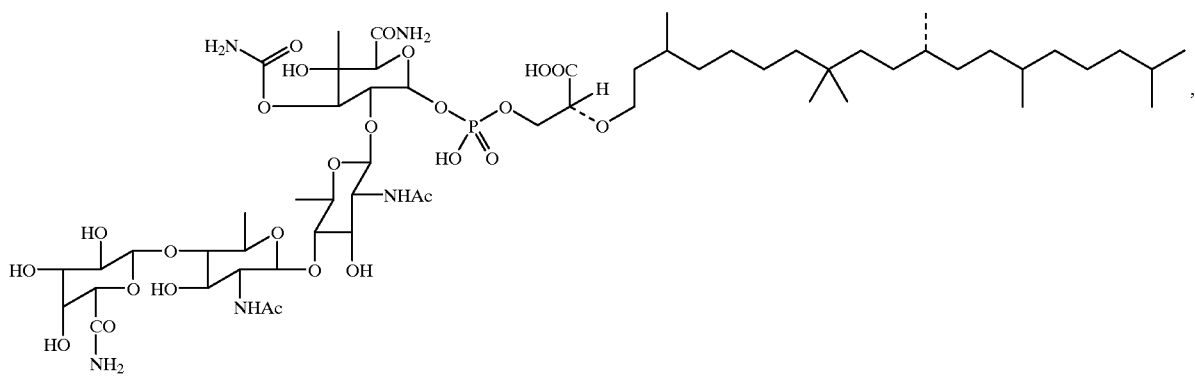

13

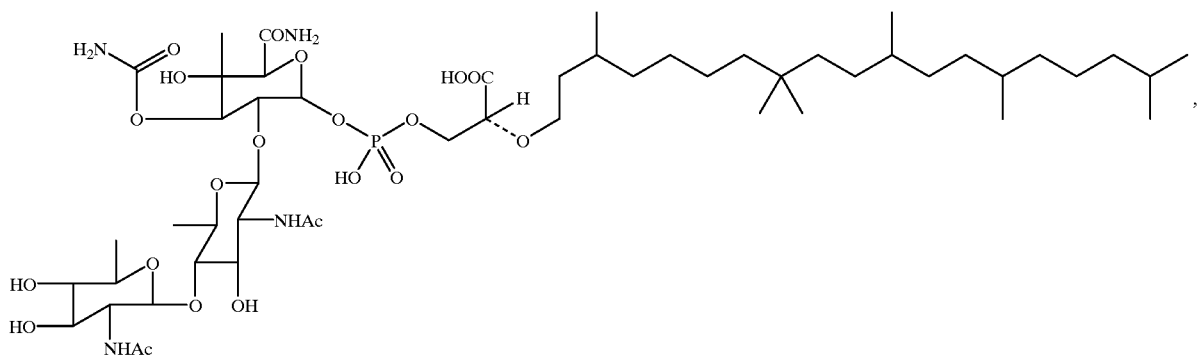

14

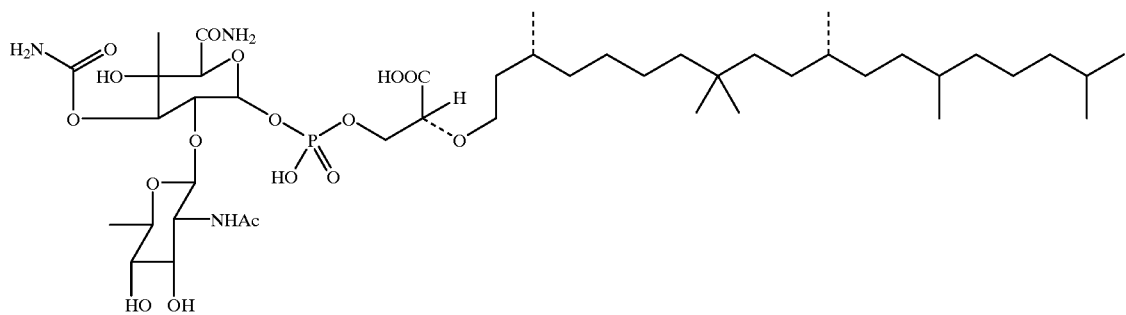

15

The compounds 11–15 represent the degradation products of moenomycin C$_3$. Analogous degradation products of the compounds 2, 4, 5 and 6 can be employed according to the invention in a similar manner.

Mixtures of said compounds are additionally particularly suitable according to the invention.

Said compounds can be prepared as described e.g. in G. Huber, loc. cit., German Offenlegungsschrift 37 04 659, Tetrahedron, Vol. 49, No. 35, pp. 7667–7678, 1993 and P. Welzel in "Antibiotics and Antiviral Compounds", VCH Weinheim, 1993.

Moreover suitable for the use according to the invention are further degradation products of moenomycin, such as the degradation products which are described in the above references, or the degradation product of the following formula

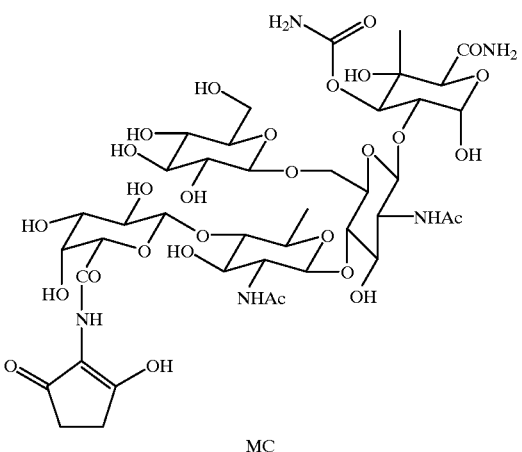

MC whose preparation is described in EP 0,355,679.

The use of moenomycin in the therapy of *H. pylori* infections has a number of advantages compared with conventional therapy:

The antibiotic is not absorbed and is excreted again almost unchanged.

Moenomycin has not been used until now in human medicine. The problem of cross-resistance with other bacterial species does not arise.

Moenomycin is extremely well tolerated. High doses can therefore be used.

Moenomycin is able to penetrate the mucus layer of the gastric mucous membrane and to reach the actual site of residence of the infecting microorganism.

Moenomycin has no antigen or hapten properties which could lead to allergies.

Further advantages in therapy with moenomycin can be achieved if the moenomycin or its derivatives are administered together with other active compounds, auxiliaries and/or excipients.

Suitable additional active compounds for said therapy are derived e.g. from the antacids group, such as e.g. sodium hydrogen carbonate, aluminum hydroxide, magnesium hydroxide, magnesium trisilicate, aluminum magnesium silicate hydrate, aluminum sodium carbonate dihydroxide, magnesium carbonate, calcium carbonate or hydrotalcite. Other suitable additional active compounds are derived from the $H_2$-receptor blocker group such as e.g. famotidine, nizatidine, roxatidine acetate, ranitidine or cimetidine. Other suitable additional active compounds are muscarin receptor blockers such as propantheline bromide, pirenzipine or other antiulcer agents such as omeprazole, lansoprazole, misoprostol or bismuth salts such as bismuth nitrate, bismuth carbonate, bismuth salicylate or bismuth citrate. Additional active compounds which are further suitable for the therapy according to the invention belong to the antibiotics group such as e.g. tetracycline, metronidazole, amoxycillin, nisin, clarithromycin, imipenem, or amikacin. The above-mentioned additional active compounds are mainly commercial products and obtainable by generally known methods (cf. Rote Liste 1993, Editio Cantor, Aulendorf, Württ., Merck Index, 11$^{th}$ Ed., Merck & Co., Rahway, N.J., 1989).

It can also be useful to carry out the moenomycin therapy using a mixture of the abovementioned additional active compounds.

The administration of moenomycin together with amoxycillin and/or metronidazole, tetracycline, omeprazole, ranitidine and/or a bismuth salt is particularly preferred.

The administration of the components of said combination preparations can take place in the form of a single administration or alternatively be performed in chronological order.

The pharmaceutical preparation of the pharmaceuticals according to the invention is carried out according to prior art methods, e.g. in the form of solutions, suspensions, capsules, tablets, treatments where the patient takes medicine, lies for five minutes on his back, five minutes on his side, then on his front etc., or the like.

The pharmaceutical compositions which contain the active compound or compounds can be in a suitable form for oral administration, for example as tablets, pastilles, lozenges, aqueous suspensions or solutions, dispersible powders or granules, emulsions, hard or soft capsules, syrup or elixir. Compositions intended for oral administration can be prepared according to any appropriate method according to the prior art for the production of pharmaceutical compositions, and these compositions can contain one or more substances from the sweeteners, flavorings, colorants and preservatives group in order to obtain a pharmaceutically elegant and readily administrable preparation.

Formulations for oral administration comprise tablets which contain the active compound in a mixture with non-toxic, pharmaceutically acceptable excipients. These excipients can be, for example, inert extenders (such as, for example, sodium chloride, lactose, calcium phosphate or sodium phosphate), granulating or disintegrants (for example potato starch, alginic acid), binders (such as, for example, starch, gelatin or gum arabic) and lubricants (such as, for example, magnesium stearate, stearic acid or talc). The tablets can be uncoated or they can be coated by means of the known techniques in order to delay dissolution and absorption in the stomach and thus to give a lasting action over a relatively long period of time. A time-delaying substance, for example, such as glyceryl monostearate or glyceryl distearate can thus be employed.

Formulations for oral administration can also be made available in the form of hard gelatin capsules in which the active compound is mixed with an inert, solid extender, for example calcium phosphate or kaolin, or in the form of soft gelatin capsules in which the active compound is mixed with water or an oily medium, for example groundnut oil, liquid paraffin or olive oil.

Of course, the therapeutic dose spectrum of the compounds according to the invention varies depending on the size and needs of the patients and the pains or disease symptoms to be treated in each case. The amount of active compound which can be combined with the excipient substances in order to form a single administration form varies depending on the host to be treated and the particular type of administration. Thus, for example, for a formulation for oral administration intended for humans, the amount is preferably between 5 mg and 5 g of the respective active compound(s), it being intended for the pharmaceutical to contain an appropriate and useful amount of excipients, which can make up between 5 and 95 % of the total composition.

It is understood that the specific dose for each individual patient is dependent on a plurality of factors, including efficacy of the specific compound which is employed, age, body weight, general state of health, sex, nutrition, administration time, administration route, excretion rate, interactions with other pharmaceuticals and severity of the disorder treated in each case.

The present invention is intended to be illustrated in greater detail by the following exemplary embodiments:

EXAMPLE 1

For the rapid determination of the activity of moenomycin, defined amounts of moenomycin in aqueous solution are added dropwise to small filter plates. After drying, the small plates are placed on nutrient agar plates which have been inoculated with *Helicobacter pylori*.

Various clinical isolates of *Helicobacter pylori* are cultured in liquid nutrient medium. The nutrient medium consists of Müller-Hinton broth, to which are added 4% fetal calf serum, 10 mg/l of vancomycin and 500 mg/l of Actidione (the last two to avoid contamination). The inoculated nutrient medium is stirred at 37° C. under specific gas conditions (Anaerocult® C) for two days. 100 µl of the bacterial suspension are spread out on the surface of the nutrient agar plate with a spatula. The nutrient agar consists of Columbia agar containing 5% wether's blood, to which 10 mg/l of vancomycin and 500 mg/l of Actidione® are in turn added. After laying on the moenomycin-containing small filter plates, the plates are incubated first for 1 h at 4° C. and then for 4 days at 37° C. under the same gas conditions as the liquid cultures.

The small plates typically contain 25, 12.5, 6.25, 3.12 etc. µg of moenomycin.

For assessment, the bacteria-free inhibition halo which surrounds a small plate after incubation is measured. The diameter of the small filter plates on their own is 6 mm.

If moenomycin A and the bacterial strain *Helicobacter pylori* P22 is used, the following result is obtained:

| [Moenomycin A] | 25 | 12.5 | 6.25 | 3.12 | 1.56 | 0.78 | 0.39 | 0.19 |
|---|---|---|---|---|---|---|---|---|
| Inhibition halo (mm) | 34 | 32 | 30 | 28 | 23 | 20 | 16 | 11 |

EXAMPLE 2

If the procedure is as described in Example 1, but a commercially available antacid (e.g. Maalox® 70 in the recommended dose) is added to the moenomycin solution before adding it dropwise to the small filter plates, the following result is obtained when using moenomycin A and the *Helicobacter pylori* strain P22:

| [Moenomycin A] | 25 | 12.5 | 6.25 | 3.12 | 1.56 | 0.78 | 0.39 | 0.19 |
|---|---|---|---|---|---|---|---|---|
| Inhibition halo (mm) | 32 | 30 | 25 | 25 | 25 | 25 | 24 | 23 |

The result indicates a potentiation of efficacy of moenomycin A by an antacid in the lower concentration range. If other *Helicobacter pylori* strains are used, similarly running curves are obtained.

EXAMPLE 3

Determination of the minimum inhibitory concentration of moenomycin A.

To determine the minimum inhibitory concentration of moenomycin A against various *Helicobacter pylori* strains in vitro, the agar dilution test, which is known to the person skilled in the art, was used. To do this, various *Helicobacter pylori* strains were grown in liquid culture, as described in Example 1. Dilutions of moenomycin A were poured into agar plates such that specific concentrations of the antibiotic were established (typically 100, 50, 25, 12.5 etc. µg/ml). With the aid of a multipoint inoculator, the same strains of *Helicobacter pylori* were inoculated onto each plate in rising concentrations and incubated as in Example 1. The concentration point at which growth was just no longer detectable was read off as the MIC (minimum inhibitory concentration) for the corresponding strain. If, for example, the *Helicobacter pylori* strains P9, P19 and M84 are used, the MIC for them is between 0.19 and 0.09 µg/ml.

What is claimed is:

1. A pharmaceutical composition which comprises effective amounts of moenomycin or a derivative thereof combined with one or both of a further active ingredient for the treatment of gastric ulcers or an additional antibiotic together with a pharmacologically acceptable carrier.

2. A method for the production of a pharmaceutical composition as claimed in claim 1 which comprises bringing moenomycin or a derivative thereof into a suitable form for administration with one or both of a further active ingredient for the treatment of gastric ulcers or an additional antibiotic together with a pharmacologically acceptable carrier.

* * * * *